(12) United States Patent
Nomura et al.

(10) Patent No.: US 7,943,582 B2
(45) Date of Patent: May 17, 2011

(54) CRYSTALLINE FORM OF 1-(β-D-GLUCOPYRANSOYL)-4-METHYL-3-[5-(4-FLUOROPHENYL)-2-THIENYLMETHYL]BENZENE HEMIHYDRATE

(75) Inventors: Sumihiro Nomura, Osaka (JP); Eiji Kawanishi, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 451 days.

(21) Appl. No.: 11/987,670

(22) Filed: Dec. 3, 2007

(65) Prior Publication Data

US 2008/0146515 A1 Jun. 19, 2008

Related U.S. Application Data

(60) Provisional application No. 60/868,426, filed on Dec. 4, 2006.

(30) Foreign Application Priority Data

Dec. 4, 2006 (JP) .................................. 2006-327019

(51) Int. Cl.
*A61K 31/7034* (2006.01)
*C07H 7/04* (2006.01)

(52) U.S. Cl. ........................................ 514/23; 536/1.11
(58) Field of Classification Search .................. None
See application file for complete search history.

(56) References Cited

U.S. PATENT DOCUMENTS

| | | | |
|---|---|---|---|
| 4,160,861 A | 7/1979 | Cole et al. |
| 4,584,369 A | 4/1986 | Klein et al. |
| 5,149,838 A | 9/1992 | Humphrey et al. |
| 5,424,406 A | 6/1995 | Tsujihara et al. |
| 5,731,292 A | 3/1998 | Tsujihara et al. |
| 5,767,094 A | 6/1998 | Tsujihara et al. |
| 5,780,483 A | 7/1998 | Widdowson et al. |
| 5,830,873 A | 11/1998 | Tsujihara et al. |
| 6,048,842 A | 4/2000 | Tsujihara et al. |
| 6,153,632 A | 11/2000 | Rieveley |
| 6,297,363 B1 | 10/2001 | Kubo et al. |
| 6,414,126 B1 | 7/2002 | Ellsworth et al. |
| 6,515,117 B2 | 2/2003 | Ellsworth et al. |
| 6,562,791 B1 | 5/2003 | Maurya et al. |
| 6,617,313 B1 | 9/2003 | Maurya et al. |
| 6,627,611 B2 | 9/2003 | Tomiyama et al. |

(Continued)

FOREIGN PATENT DOCUMENTS

CA 2494177 A1 2/2004

(Continued)

OTHER PUBLICATIONS

Ahmad et al., "Synthesis and Structure Determination of Some Oxadiazole-2-Thione and Triazole-3-Thione Galactosides", Nucleosides, Nucleotides & Nucleic Acids, vol. 20, No. 9, 2001, pp. 1671-1682.

(Continued)

*Primary Examiner* — Eric S Olson
(74) *Attorney, Agent, or Firm* — Birch, Stewart, Kolasch & Birch, LLP

(57) ABSTRACT

A novel crystal form of 1-(β-D-glucopyranosyl)-4-methyl-3-[5-(4-fluorophenyl)-2-thienylmethyl]benzene hemihydrate, and having favorable characteristics, is characterized by its x-ray powder diffraction pattern and/or by its infra-red spectrum.

7 Claims, 2 Drawing Sheets

U.S. PATENT DOCUMENTS

| | | | |
|---|---|---|---|
| 7,375,213 B2 | 5/2008 | Deshpande et al. | |
| 7,511,022 B2 | 3/2009 | Beavers et al. | |
| 2001/0041674 A1 | 11/2001 | Tomiyama et al. | |
| 2002/0032164 A1 | 3/2002 | Dale et al. | |
| 2002/0052326 A1 | 5/2002 | Washburn | |
| 2002/0111315 A1 | 8/2002 | Washburn et al. | |
| 2003/0024914 A1 | 2/2003 | Aleshin | |
| 2003/0064935 A1 | 4/2003 | Gougoutas | |
| 2003/0087843 A1 | 5/2003 | Washburn | |
| 2003/0114390 A1 | 6/2003 | Washburn et al. | |
| 2004/0053855 A1 | 3/2004 | Fujikura et al. | |
| 2004/0063646 A1 | 4/2004 | Fujikura et al. | |
| 2004/0110936 A1 | 6/2004 | Ohsumi et al. | |
| 2004/0116357 A1 | 6/2004 | Fushimi et al. | |
| 2004/0132669 A1 | 7/2004 | Nishimura et al. | |
| 2004/0138143 A1 | 7/2004 | Glombik et al. | |
| 2004/0259819 A1 | 12/2004 | Frick et al. | |
| 2005/0014704 A1 | 1/2005 | Frick et al. | |
| 2005/0032711 A1 | 2/2005 | Patel et al. | |
| 2005/0032712 A1 | 2/2005 | Urbanski | |
| 2005/0037980 A1 | 2/2005 | Rybczynski et al. | |
| 2005/0037981 A1 | 2/2005 | Beavers et al. | |
| 2005/0124556 A1 | 6/2005 | Burton | |
| 2005/0233988 A1* | 10/2005 | Nomura et al. | 514/43 |
| 2006/0217323 A1 | 9/2006 | Patel et al. | |
| 2006/0229260 A1 | 10/2006 | Rybczynski et al. | |
| 2006/0234954 A1 | 10/2006 | Urbanski | |
| 2006/0293251 A1 | 12/2006 | Urbanski et al. | |
| 2007/0060545 A1 | 3/2007 | Nomura et al. | |

FOREIGN PATENT DOCUMENTS

| | | |
|---|---|---|
| EP | 0355750 A1 | 2/1990 |
| EP | 0579204 A3 | 1/1994 |
| EP | 1338603 A1 | 8/2003 |
| EP | 1528066 A1 | 5/2005 |
| GB | 2359554 A | 8/2001 |
| JP | 63-233975 A | 9/1988 |
| JP | 4-253974 A | 9/1992 |
| JP | 9-263549 A | 10/1997 |
| JP | 10-324632 A | 12/1998 |
| JP | 2000-34230 A | 2/2000 |
| JP | 2000-34239 A | 2/2000 |
| JP | 2001-288178 A | 10/2001 |
| JP | 2003-12686 A | 1/2003 |
| WO | WO 93/21178 A1 | 10/1993 |
| WO | WO 97/25033 A1 | 7/1997 |
| WO | WO 00/74681 A1 | 12/2000 |
| WO | WO 01/27128 A1 | 4/2001 |
| WO | WO 01/64669 A1 | 9/2001 |
| WO | WO 01/68660 A1 | 9/2001 |
| WO | WO 01/74834 A1 | 10/2001 |
| WO | WO 01/74835 A1 | 10/2001 |
| WO | WO 02/053573 A1 | 7/2002 |
| WO | WO 02/068439 A1 | 9/2002 |
| WO | WO 02/068440 A1 | 9/2002 |
| WO | WO 02/070020 A2 | 9/2002 |
| WO | WO 02/083066 A2 | 10/2002 |
| WO | WO 02/088157 A1 | 11/2002 |
| WO | WO 02/094262 A1 | 11/2002 |
| WO | WO 03/000712 A1 | 1/2003 |
| WO | WO 03/011880 A1 | 2/2003 |
| WO | WO 03/020737 A1 | 3/2003 |
| WO | WO 03/043621 A1 | 5/2003 |
| WO | WO 03/087104 A1 | 10/2003 |
| WO | WO 03/099836 A1 | 12/2003 |
| WO | WO 2004/007517 A | 1/2004 |
| WO | WO 2004/013118 A | 2/2004 |
| WO | WO 2004/014931 A1 | 2/2004 |
| WO | WO 2004/018442 A1 | 3/2004 |
| WO | WO 2004/019958 A1 | 3/2004 |
| WO | WO 2004/052902 A1 | 6/2004 |
| WO | WO 2004/052903 A1 | 6/2004 |
| WO | WO 2004/063209 A2 | 7/2004 |
| WO | WO 2004/080990 A1 | 9/2004 |
| WO | WO 2004/087727 A1 | 10/2004 |
| WO | WO 2004/099230 A1 | 11/2004 |
| WO | WO 2004/113359 A1 | 12/2004 |
| WO | WO-2005/012326 A1 | 2/2005 |
| WO | WO 2005/030127 A2 | 4/2005 |
| WO | WO 2006/108842 A1 | 10/2006 |
| WO | WO 2006/120208 A1 | 11/2006 |
| WO | WO 2007/035198 A2 | 3/2007 |
| WO | WO 2007/054978 A2 | 5/2007 |
| WO | WO 2007/107354 A1 | 9/2007 |

OTHER PUBLICATIONS

Appleton et al., "A Mild and Selective C-3 Reductive Alkylation of Indoles", Tetrahedron Letters, vol. 34, No. 9, 1993, pp. 1529-1532.

Arakawa et al, "Improved diabetic syndrome in C57BL/KsJ-db/db mice by oral administration of the Na+ -glucose cotransporter inhibitor T-1095," British Journal of Pharmacology, vol. 132, 2001, pp. 578-586.

Banker et al. (Editors), Modern Pharmaceutics, Third Edition, published 1996, p. 596, Marcel Dekker, Inc.

Benhaddou et al.,"Tetra-n-propylammonium tetra-oxoruthenate(VII): a reagent of choice for the oxidation of diversely protected glycopyranoses and glycofuranoses to lactones", Carbohydrate Research, vol. 260, 1994, pp. 243-250.

Bertolini et al., "A New Simple One-Pot Regioselective Preparation of Mixed Diesters of Carbonic Acid.", Journal of Organic Chemistry, vol. 63, No. 17, 1998, pp. 6031-6034.

Blair et al., "Effect of Ring Fluorination on the Pharmacology of Hallucinogenic Tryptamines", J. Med. Chem., vol. 43, 2000, pp. 4701-4710.

Boehm et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem., vol. 43, No. 14, 2000, pp. 2664-2674.

Brooks et al., "Boron Trichloride/Tetra-n-Butylammonium Iodide: A Mild, Selective Combination Reagent for the Cleavage of Primary Alkyl Aryl Ethers", J. Org. Chem., vol. 64, 1999, pp. 9719-9721.

CAS Reg. No. 487001-40-1, IPOrganisers, Entered STN Feb. 7, 2003, pp. 1-2.

Comins et al., "Synthesis of 3-Substituted Indoles Via N-Acylindolium Ions", Tetrahedron Letters, vol. 27, No. 17, 1986, pp. 1869-1872.

Czernecki et al., "C-Glycosides. 7. Stereospecific C-Glycosylation of Aromatic and Heterocyclic Rings", J. Org. Chem., vol. 54, 1989, pp. 610-612.

Deeg et al., "Pioglitazone and Rosiglitazone Have Different Effects on Serum Lipoprotein Particle Concentrations and Sizes in Patients With Type 2 Diabetes and Dyslipidemia.", Diabetes Care, vol. 30, No. 10, Oct. 2007, pp. 2458-2464.

Deetjen et al., "Renal Handling of D-Glucose and Other Sugars", Textbook of Nephrology, vol. 1, 3rd Edition, 1995, pp. 90-94.

Devivar et al., "Benzimidazole Ribonucleosides: Design, Synthesis, and Antiviral Activity of Certain 2-(Alkylthio)- and 2-(Benzylthio)-5,6-dichloro-1-(β-D-ribofuranosyl)benzimidazoles1," J.Med. Chem., vol. 37, 1994, pp. 2942-2949.

Dewynter et al., "Synthesis of Pseudonucleosides containing Chiral Sulfahydantoins as Aglycone (II)", Tetrahedron, vol. 52, No. 3, 1996, pp. 993-1004.

Dillard et al., "Indole Inhibitors of Human Nonpancreatic Secretory Phospholipase A2. 1. Indole-3-acetamides", J. Med. Chem., vol. 39, 1996, pp. 5119-5136.

Dondoni et al., "Stereoselective synthesis of C-glycosylphosphonates from their ketols. Reconsideration of an abandoned route", Tetrahedron: Asymmetry, vol. 11, 2000, pp. 305-317.

Dondoni et al., "Thiazole-Based Synthesis of Formyl C-Glycosides", J. Org. Chem., vol. 59, 1994, pp. 6404-6412.

Dudash, Jr. et al, "Glycosylated dihydrochalcones as potent and selective sodium glucose co-transporter 2 (SGLT2) inhibitors," Bioorganic & Medicinal Chemistry Letters, vol. 14, 2004, pp. 5121-5125.

Dunn et al., "Analgetic and antiinflammatory 7-Aroylbenzofuran-5-ylacetic acids and 7-Aroylbenzothiophene-5-ylacetic Acids.", Journal of Med. Chem., vol. 29, No. 1, 1986, pp. 2326-2329.

Eid et al., "Reaction of Some 1,2,4-Triazines with Acetobromoglucose", Arch. Pharm. (Weinheim), vol. 323, 1990, pp. 243-245.

Ellsworth et al, "Aglycone exploration of C-arylglucoside inhibitors of renal sodium-dependent glucose transporter SGLT2," Bioorganic & Medicinal Chemistry Letters, vol. 18, 2008, pp. 4770-4773.

Ellsworth et al., "C-Arylglucoside synthesis: triisopropylsilane as a selective reagent for the reduction of an anomeric C-phenyl ketal," Tetrahedron: Asymmetry, vol. 14, 2003, pp. 3243-3247.

Fresneda et al., "Synthesis of the indole alkaloids meridianins from the tunicate Aplidium meridianum," Tetrahedron, vol. 57, 2001, pp. 2355-2363.

Gershell, "Type 2 diabetes market", Nature Reviews Drug Discovery, vol. 4, May 2005, pp. 367-368.

Goodman & Gilman's The Pharmacological Basis of Therapeutics, 10th Edition, McGraw-Hill Medical Publishing Division, 2001, pp. 54-57.

Han et al., "Dapagliflozin, a Selective SGLT2 Inhibitor, Improves Glucose Homeostasis in Normal and Diabetic Rats", Diabetes, vol. 57, Jun. 2008, pp. 1723-1729.

Handlon, "Sodium glucose co-transporter 2 (SGLT2) inhibitors as potential antidiabetic agents," Expert Opin. Ther. Patents, vol. 15, No. 11, 2005, pp. 1531-1540.

Hofslokken et al., "Convenient Method for the ortho-Formylation of Phenols.", Acta Chemica Scandinavica, vol. 53, 1999, pp. 258-262.

Hongu et al., "Na+-Glucose Cotransporter Inhibitors as Antidiabetic Agents. II.1) Synthesis and Structure-Activity Relationships of 4'-Dehydroxyphlorizin Derivatives", Chem. Pharm. Bull., vol. 46, No. 1, 1998, pp. 22-33.

Horton et al., "Synthetic Routes to Higher-Carbon Sugars. Reaction of Lactones with 2-Lithio-1,3-Dithiane", Carbohydrate Research, vol. 94, 1981, pp. 27-41.

Hu et al., "A New Approach Towards the Yellowing Inhibition of Mechanical Pulps. Part I: Selective Removal of alpha-Hydroxyl and alpha-Carbonyl Groups in Lignin Model Compounds", Holzforschung, vol. 53, No. 1, 1999, pp. 43-48.

Huang-Minlon, "Reduction of Steroid Ketones and other Carbonyl Compounds by Modified Wolff-Kishner Method", J. Am. Chem. Soc., vol. 71, Oct. 1949, pp. 3301-3303.

Ibrahim et al., "Selective Synthesis and Structure of 2-N- and 3-S-Glucosyl-1,2,4-Triazoles of Potential Biological Interest", Carbohydrate Letters, vol. 3, No. 5, 1999, pp. 331-338.

Ibrahim, "Facile Approach for the Selective Glycosidation of Cyclic Asymmetric Amides and Thioamides", Carbohydrate Letters, vol. 1, 1996, pp. 425-432.

Information Submission of Sep. 1, 2009 in U.S. Appl. No. 11/045,446, including Appendices A, B and C.

International Search Report for Application No. PCT/JP2004/011312, dated Nov. 25, 2004.

Isaji, "Sodium-glucose cotransporter inhibitor for diabetes," Current Opinion in Investigational Drugs, vol. 8, No. 4, 2007, pp. 285-292.

Kahn et al, "Normalization of Blood Glucose in Diabetic Rats with Phlorizin Treatment Reverses Insulin-resistant Glucose Transport in Adipose Cells without Restoring Glucose Transporter Gene Expression," J. Clin. Invest., vol. 87, Feb. 1991, pp. 561-570.

Kanai et al., "The Human Kidney Low Affinity Na+/Glucose Cotransporter SGLT2: Delineation of the Major Renal Reabsorptive Mechanism for D-Glucose", J. Clin. Invest., vol. 93, Jan. 1994, pp. 397-404.

Kasahara et al., "A missense mutation in the Na+/glucose cotransporter gene SGLT1 in a patient with congenital glucose-galactose malabsorption: normal trafficking but inactivation of the mutant protein," Biochimica et Biophysica Acta, vol. 1536, 2001, pp. 141-147.

Katz et al., "Quantitative Insulin Sensitivity Check Index: A Simple, Accurate Method for Assessing Insulin Sensitivity In Humans.", J. of Clin. Endocrinology & Metabolism, vol. 85, No. 7, 2000, pp. 2402-2410.

Ketcha et al., "Synthesis of Alyl-Substituted N-Protected Indoles via Acylation and Reductive Deoxygenation1" J. Org. Chem., vol. 54, 1989, pp. 4350-4356.

Khan et al, "Reactions of Phenyl-Substituted Heterocyclic Compounds—II. Nitrations and Brominations of 1-Phenylpyrazole Derivatives," Canadian Journal of Chemistry, vol. 41, 1963, pp. 1540-1547.

Liang et al., "JNJ-28431754/TA-7284, an Inhibitor of Sodium-Glucose Cotransporter 2, Ameliorates Diabetic Syndrome in the Zucker Diabetic Fatty Rat," Oct. 2009, Poster presented at International Diabetes Federation 20th World Diabetes Congress, Montreal, Canada.

Liang et al., "JNJ-28431754/TA-7284, an Inhibitor of Sodium-Glucose Cotransporter 2, Reduces Body Weight Gain in Zucker Fatty Rats," Oct. 2009, Poster presented at International Diabetes Federation 20th World Diabetes Congress, Montreal, Canada.

Liang et al., "JNJ-28431754/TA-7284, an SGLT Inhibitor, Lowers Blood Glucose and Reduces Body Weight in Obese and type 2 Diabetic Animal Models," Jun. 2009.

Lin et al., "Syntheses of Guanidinoglycosides with the Inventive use of Mitsunobu Conditions and 1, 8-Diazabicyclo[5.4.0]undec-7-ene.", Synthesis, No. 2, 2003, pp. 255-261.

Link et al., "A method for preparing C-glycosides related to phlorizin" Tetrahedron Letters, vol. 41, 2000, pp. 9213-9217.

Lipscombe et al., "Trends in diabetes prevalence, incidence, and mortality in Ontario, Canada 1995-2005: a population-based study", Lancet, vol. 369, 2007, pp. 750-756.

Maatooq, "C-p-Hydroxybenzoylglycoflavones from Citrullus Colocynthis", Phytochemistry, vol. 44, No. 1, Jan. 1997, pp. 187-190.

Mackenzie et al., "Biophysical Characteristics of the Pig Kidney Na+/Glucose Cotransporter SGLT2 Reveal a Common Mechanism for SGLT1 and SGLT2", J. Biol. Chem., vol. 271, No. 5, 1996, pp. 32678-32683.

Manis et al., "Metabolism of 4,4'-Methylenebis(2-chloroaniline) By Canine Liver and Kidney Slices.", Drug Metabolism and Disposition, vol. 14, No. 2, 1986, pp. 166-174.

Marsenic, "Glucose Control by the Kidney: An Emerging Target in Diabetes.", Am. J. of Kidney Diseases, vol. 53, No. 5, May 2009, pp. 875-883.

Matsuda et al., "Insulin Sensitivity Indices Obtained From Oral Glucose Tolerance Testing: Comparison with the euglycemic insulin clamp," Diabetes Care, vol. 22, No. 9, Sep. 1999, pp. 1462-1470.

Matthews et al., "Homeostasis model assessment: insulin resistance and β-cell function from fasting plasma glucose and insulin concentrations in man," Diabetolgia, vol. 28, 1985, pp. 412-419.

Meanwell et al., "Regiospecific Functionalization of 1,3-Dihydro-2H-benzimidazol-2-one and Structurally Related Cyclic Urea Derivates.", J. Org. Chemistry, vol. 60, No. 6, 1995, pp. 1565-1582.

Meng et al., "Discovery of Dapagliflozin: A Potent, Selective Renal Sodium-Dependent Glucose Cotransporter 2 (SGLT2) Inhibitor for the Treatment of Type 2 Diabetes", J. Med. Chem., vol. 51, No. 5, 2008, pp. 1145-1149.

Mewshaw et al., "New Generation Dopaminergic Agents. 7. Heterocyclic Bioisosteres that Exploit the 3-OH-Phenoxyethylamine D2 Template", Bioorganic & Medicinal Chemistry Letters, vol. 9, 1999, pp. 2593-2598.

Miyaura et al., "Palladium-Catalyzed Cross-Coupling Reactions of Organoboron Compounds.", Chem. Rev., vol. 95, No. 7, 1995, pp. 2457-2483.

Nishimura et al, "Tissue-specific mRNA Expression Profiles of Human ATP-binding Cassette and Solute Carrier Transporter Superfamilies," Drug Metab. Pharmacokinet., vol. 20, No. 6, 2005, pp. 452-477.

Nomura et al., "Discovery of Novel C-glucosides with Thiophene Ring as Sodium-dependent Glucose Cotransporter 2 Inhibitors for the Treatment of Type 2 Diabetes Mellitus", MEDI 151, Abstract, The 238th ACS National Meeting, Washington, DC, Aug. 16-20, 2009; American Chemical Society: Washington, DC.

Nomura, "Renal Sodium-Dependent Glucose Cotransporter 2 (SGLT2) Inhibitors for New Anti-Diabetic Agent," Current Topics in Medicinal Chemistry, vol. 10, No. 4, 2010, pp. 411-418.

Office Action in U.S. Appl. No. 11/045,446, dated Dec. 5, 2008.
Office Action in U.S. Appl. No. 11/045,446, dated Jun. 16, 2008.
Office Action in U.S. Appl. No. 11/045,446, dated Oct. 1, 2009.

Ohsumi et al. "Pyrazole-O-Glucosides as Novel Na+-Glucose Cotransporter (SGLT) Inhibitors" Bioorganic & Medicinal Chemistry Letters, vol. 13, 2003, pp. 2269-2272.

Oku et al., "T-1095, an Inhibitor of Renal Na+-Glucose Cotransporters, May Provide a Novel Approach to Treating Diabetes", Diabetes, vol. 48, Sep. 1999, pp. 1794-1800.

Orjales et al. "New 2-Piperazinylbenzimidazole Derivatives as 5-HT-3 Antagonists. Synthesis and Pharmacological Evaluation," J. Med. Chem., vol. 40, 1997, pp. 586-593.

Patani et al., "Bioisosterism: A Rational Approach to Drug Design", Chem. Rev., American Chemical Society, vol. 96, 1996, pp. 3147-3176.

Peng et al., "Post-transcriptional Regulaton of Na+/Glucose Cotransporter (SGTL1) Gene Expression in LLC-PK1 Cells.", Journal of Biological Chemistry, vol. 270, No. 35, 1995, pp. 20536-20542.

Polidori et al., "Frequently Used Insulin Sensitivity Measures May Be Inappropriate for Subjects Treated With SGLT2 Inhibitors," Jun. 2009, Poster presented at the American Diabetes Assoc. 69th Scientific Sessions, Jun. 5-9, 2009, New Orleans, LA.

Raynaud et al., "Revised Concept for the Estimation of Insulin Sensitivity From a Single Sample.", Diabetes Care, vol. 22, No. 6, Jun. 1999, pp. 1003-1004.

Rossetti et al, "Correction of Hyperglycemia with Phlorizin Normalizes Tissue Sensitivity to Insulin in Diabetic Rats," J. Clin. Invest., vol. 79, May 1987, pp. 1510-1515.

Rossetti et al, "Effect of Chronic Hyperglycemia on in Vivo Insulin Secretion in Partially Pancreatectomized Rats," J. Clin. Invest., vol. 80, Oct. 1987, pp. 1037-1044.

Rossetti et al., "Glucose Toxicity," Diabetes Care, vol. 13, Issue 6, 1990, pp. 610-630, Abstract only.

Silverman, "The Organic Chemistry of Drug Design and Drug Action," Academic Press, 1992, pp. 19-23.

Somei et al., "The First and Simple Total Synthesis of Cappariloside A1," Heterocycles, vol. 53, No. 7, 2000, pp. 1573-1578.

Srogl et al., "Sulfonium Salts. Participants par Excellence in Metal-Catalyzed Carbon-Carbon Bond-Forming Reactions", J. Am. Chem. Soc., vol. 119, No. 50, 1997, pp. 12376-12377.

Stoner et al, "Benzylation via Tandem Grignard Reaction—Iodotrimethylsilane (TMSI) Mediated Reduction," Tetrahedron, vol. 51, No. 41, 1995, pp. 11043-11062.

Stumvoll et at "Use of the Oral Glucose Tolerance Test to Assess Insulin Release and Insulin Sensitivity.", Diabetes Care, vol. 23, No. 3, Mar. 2000, pp. 295-301.

Tanaka et al. "Solid-Phase Synthesis of β-Mono-Substituted Ketones and an Application to the Synthesis of a Library of Phlorizin Derivatives", Synlett, No. 9, 2002, pp. 1427-1430.

The State Intellectual Property Office of P.R. China Office Action, Appl. No. 2004800220078, Dec. 26, 2008, pp. 1-6, Second Office Action, English translation.

The State Intellectual Property Office of P.R. China Office Action, Appl. No. 2004800220078, Oct. 19, 2007, pp. 1-6, First Office Action, English translation.

The State Intellectual Property Office of P.R. China The Decision of Rejection (PCT) Action, Appl. No. 2004800220078, Nov. 2009, pp. 1-7.

The State Intellectual Property Office of P.R. China, Observations (1st), Appl. No. 2004800220078, May 2008, pp. 1-3, English translation.

The State Intellectual Property Office of P.R. China, Observations (2nd), Appl. No. 2004800220078, May 2009, pp. 1-4, English translation.

The State Intellectual Property Office of P.R. China, Record of Interview, Appl. No. 2004800220078, Sep. 2009, pp. 1-7, English translation.

The State Intellectual Property Office of P.R. China, Response to The Decision of Rejection (PCT), Appl. No. 2004800220078, Feb. 2010, pp. 1-27, English translation.

Thornber, "Isosterism and Molecular Modification in Drug Design", Chemical Society Reviews, vol. 8, 1979, pp. 563-580.

Tsujihara et al, "Na+-Glucose Cotransporter (SGLT) Inhibitors as Antidiabetic Agents. 4. Synthesis and Pharmacological Properties of 4'-Dehydroxyphlorizin Derivatives Substituted on the B Ring," J. Med. Chem., vol. 42, No. 26, 1999, pp. 5311-5324.

Tsujihara et al., "Na+-Glucose Cotransporter Inhibitors as Antidiabetic.I. Synthesis and Pharmacological Properties of 4'-Dehydroxyphlorizin Derivatives Based on a New Concept," Chem. Pharm. Bull., vol. 44, No. 6, 1996, pp. 1174-1180.

Tsujihara et al., Bio Clinica, vol. 13, No. 4, 1998, pp. 324-328, English language Abstract.

Turk et al., "Glucose/galactose malabsorption caused by a defect in the Na+/glucose cotransporter," Nature, vol. 350, Mar. 1991, pp. 354-356.

Ueta et al, "Anti-diabetic and Anti-obesity effects of TA-7284, a Novel SGLT2 Inhibitor," Partial English translation, JDS Poster Presentation, 2009.

Ueta et al, "Long-term treatment with the Na+-glucose cotransporter inhibitor T-1095 causes sustained improvement in hyperglycemia and prevents diabetic neuropathy in Goto-Kakizaki Rats," Life Sciences, vol. 76, 2005, pp. 2655-2668.

Unger et al., "Hyperglycaemia as an inducer as well as a consequence of impaired islet cell function and insulin resistance: implications for the management of diabetes.", Diabetologia, vol. 28, 1985, pp. 119-121.

Wallace et al., "Use and Abuse of HOMA Modeling.", Diabetes Care, vol. 27, No. 6, Jun. 2004, pp. 1487-1495.

Wang et al, "Selective monolithiation of 2,5-dibromopyridine with butyllithium," Tetrahedron Letters, vol. 41, 2000, pp. 4335-4338.

Wareham et al., "Is There Really an epidemic of diabetes?", Diabetologia, vol. 48, 2005, pp. 1454-1455.

Washburn, "Evolution of sodium glucose co-transporter 2 inhibitors as anti-diabetic agents," Expert Opin. Ther. Patents, vol. 19, No. 11, 2009, pp. 1485-1499.

Wild et al., "Global Prevalence of Diabetes: Estimates for the year 2000 and projections for 2030," Diabetes Care, vol. 27, No. 5, May 2004, pp. 1047-1053.

Wolff, vol. 1: Principles and Practice, Burger's Medicinal Chemistry and Drug Discovery, 5th Edition, 1995, pp. 975-977.

Wright, "Renal Na+-glucose cotransporters," Am J Physiol Renal Physiol, vol. 280, 2001, pp. F10-F18.

Yang et al., "Convergent C-Glycolipid Synthesis via the Ramberg-Bäcklund Reaction: Active Antiproliferative Glycolipids", vol. 1, No. 13, Org. Lett. 1999, pp. 2149-2151.

Zamani, "Synthesis and Structure Determination of Some New N-Glycosides of 4,5-Disubstituted-1,2,4-triazole-3-thiones", Journal of the Chinese Chemical Society, vol. 49, 2002, pp. 1041-1044.

Zhou, "The Synthesis and Characterization of 1-Benzyl-3-N-(Beta-D-glucoside-1-yl)-5-fluorouracil", Hecheng Huaxue, vol. 9, No. 3, 2001, pp. 272-274.

Amishiro, N. et al., "Synthesis and Antitumor Activity of Duocarmycin Derivatives: A-Ring Pyrrole Compounds Bearing 5-Membered Heteroarylacryloyl Groups," Chem. Pharm. Bull., Oct. 1999, vol. 47, No. 10, pp. 1393-1403.

Bookser, B.C., "2-Benzyloxymethyl-5-(tributylstannyl)tetrazole. A reagent for the preparation of 5-aryl- and 5-heteroaryl-1H-tetrazoles via the Stille reaction," Tetrahedron Letters, 2000, vol. 41, pp. 2805-2809.

Bouillon, A. et al, "Synthesis of novel halopyridinylboronic acids and esters. Part 2: 2,4, or 5-Halopyridin-3-yl-boronic acids and esters," Tetrahedron, 2002, vol. 58, pp. 3323-3328.

Bouillon, A. et al, "Synthesis of novel halopyridinylboronic acids and esters. Part 3: 2, or 3-Halopyridin-4-yl-boronic acids and esters," Tetrahedron, 2002, vol. 58, pp. 4369-4373.

Bouillon, A. et al, "Synthesis of novel halopyridinylboronic acids and esters. Part 4: Halopyridin-2-yl-boronic acids and esters are stable, crystalline partners for classical Suzuki cross-coupling," Tetrahedron, 2003, vol. 59, pp. 10043-10049.

Cicchillo, R.M. et al, "A convenient synthesis of glycosyl chlorides from sugar hemiacetals using triphosgene as the chlorine source," Carbohydrate Research, 2000, vol. 328, pp. 431-434.

Clayden, J. et al, "Dearomatizing Cyclization of Arylsulfonylalkoxymethyl Lithiums: A Route to the Podophyllotoxin Skeleton," Organic Letters, 2003, vol. 5, No. 6, pp. 831-834.

Cottet, F. et al, "Recommendable Routes to Trifluoromethyl-Substituted Pyridine- and Quinolinecarboxylic Acids," Eur. J. Org. Chem., 2003, pp. 1559-1568.

De Las Heras, F. G. et al, "Alkylating Nucleosides 1. Synthesis and Cytostatic Activity of N-Glycosyl(halomethyl)-1,2,3-triazoles. A New Type of Alkylating Agent," Journal of Medicinal Chemistry, 1979, vol. 22, No. 5, pp. 496-501.

Frahn, J. et al, "Functionalized AB-Type Monomers for Suzuki Polycondensation," Synthesis, Nov. 1997, pp. 1301-1304.

Fuller, L.S. et al, "Thienothiophenes. Part 2. Synthesis, metallation and bromine-lithium exchange reactions of thieno[3,2-b-thiophene and its polybromo derivatives," J. Chem. Soc., Perkin Trans. 1., 1997, pp. 3465-3470.

Ganesh, T. et al, "Synthesis and biological evaluation of fluorescently labeled epothilone analogs for tubulin binding studies," Tetrahedron, 2003, vol. 59, pp. 9979-9984.

Gohier, F. et al, "ortho-Metalation of Unprotected 3-Bromo and 3-Chlorobenzoic Acids with Hindered Lithium Dialkylamides," J. Org. Chem., 2003, vol. 68, pp. 2030-2033.

Gronowitz, S. et al, "Some Substitution Reactions of 1-(2-Thienyl)pyrazole and 1-(3'-Thienyl)pyrazole," Chemica Scripta., 1979, vol. 13, pp. 157-161.

Gros, P. et al, "Efficient and Regioselective Access to Bis-heterocycles via Palladium-Catalysed Coupling of Organostannanes and Organozincates Derived from C-6 Lithiated 2-Methoxypyridine," Synthesis, 1999, No. 5, pp. 754-756.

Lee, J. S. et al, "Synthesis and In Vitro Activity of Novel Isoxazolyl Tetrahydropyridinyl Oxazolidinone Antibacterial Agents," Bioorganic & Medicinal Chemistry Letters, 2003, vol. 13, pp. 4117-4120.

Messaoudi, S. et al, "Synthesis and biological evaluation of oxindoles and benzimidazolinones derivatives," European Journal of Medicinal Chemistry, 2004, vol. 39, pp. 453-458.

Parker, K. A. et al, "Reductive Aromatization of Quinols: Synthesis of the C-Arylglycoside Nucleus of the Paulacandins and Chaetiacandin," Organic Letters, 2000, vol. 2, No. 4, pp. 497-499.

Schmidt, R. R. et al, "Synthese von Pyrazol-, Pyrazolo[3,4-d]pyrimidin-und 1H-1,2,4-Triazolgluconucleosiden aus Glucosehydrazonen," Liebigs Ann. Chem., 1981, pp. 2309-2317.

Tilak, B.D. et al, "Carcinogenesis by Thiophene Isosters of Polycyclic Hydrocarbons," Tetrahedron, 1960, vol. 9, pp. 76-95.

Yoshimura, H. et al, "Discovery of Novel and Potent Retinoic Acid Receptor alpha-Agonists: Synthesis and Evaluation of Benzofuranyl-pyrrole and Benzothiophenyl-pyrrole Derivatives," J. Med. Chem., 2000, vol. 43, pp. 2929-2937.

* cited by examiner

CRYSTALLINE FORM OF 1-(β-D-GLUCOPYRANSOYL)-4-METHYL-3-[5-(4-FLUOROPHENYL)-2-THIENYLMETHYL]BENZENE HEMIHYDRATE

BACKGROUND OF THE INVENTION

1. Field of the Invention

This invention relates to a crystalline form of 1-(β-D-glucopyranosyl)-4-methyl-3-[5-(4-fluorophenyl)-2-thienylmethyl]benzene hemihydrate useful as an inhibitor of sodium-dependent glucose transporter, to methods for its preparation and isolation, to pharmaceutical compositions which include the compound and a pharmaceutically acceptable carrier, and to pharmaceutical methods of treatment.

2. Description of the Related Art

WO 2005/012326 pamphlet discloses a class of compounds that are inhibitors of sodium-dependent glucose transporter (SGLT) and thus of therapeutic use for treatment of diabetes, obesity, diabetic complications, and the like. There is described in WO 2005/012326 pamphlet 1-(β-D-glucopyranosyl)-4-methyl-3-[5-(4-fluorophenyl)-2-thienylmethyl]benzene of formula (I):

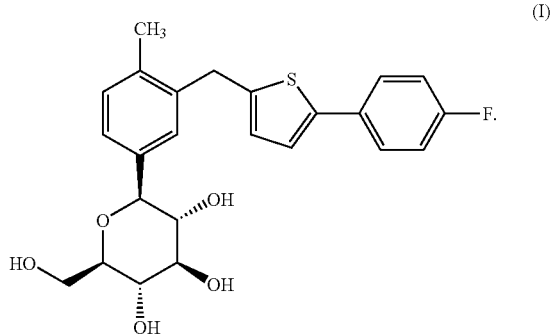

(I)

In general, for commercial use it is important that a product should have good handling qualities. Additionally, there is a need to produce the product in a pure and crystalline form to enable formulations to meet exacting pharmaceutical requirements and specifications.

And it is desirable that the product should be in a form that is readily filterable and easily dried.

Additionally, it is economically desirable that the product be stable for extended periods of time without the need for specialized storage conditions.

But there have been difficulties in obtaining a crystal form of the compound of formula (I) from organic solvents.

It has now been discovered that the compound of formula (I) hemihydrate can be produced in a crystalline form in a manner reproducible on a commercial scale.

SUMMARY OF THE INVENTION

The present invention provides a crystalline form of hemihydrate of the compound of formula (I) as a novel material, in particular in pharmaceutically acceptable form.

DETAILED DESCRIPTION OF THE INVENTION

The inventors of the present invention have found that the compounds of formula (I) can be crystallized from a water-containing solvent and the crystalline form of hemihydrate of the compounds (I) have good handling qualities and characteristics.

Figure 1:
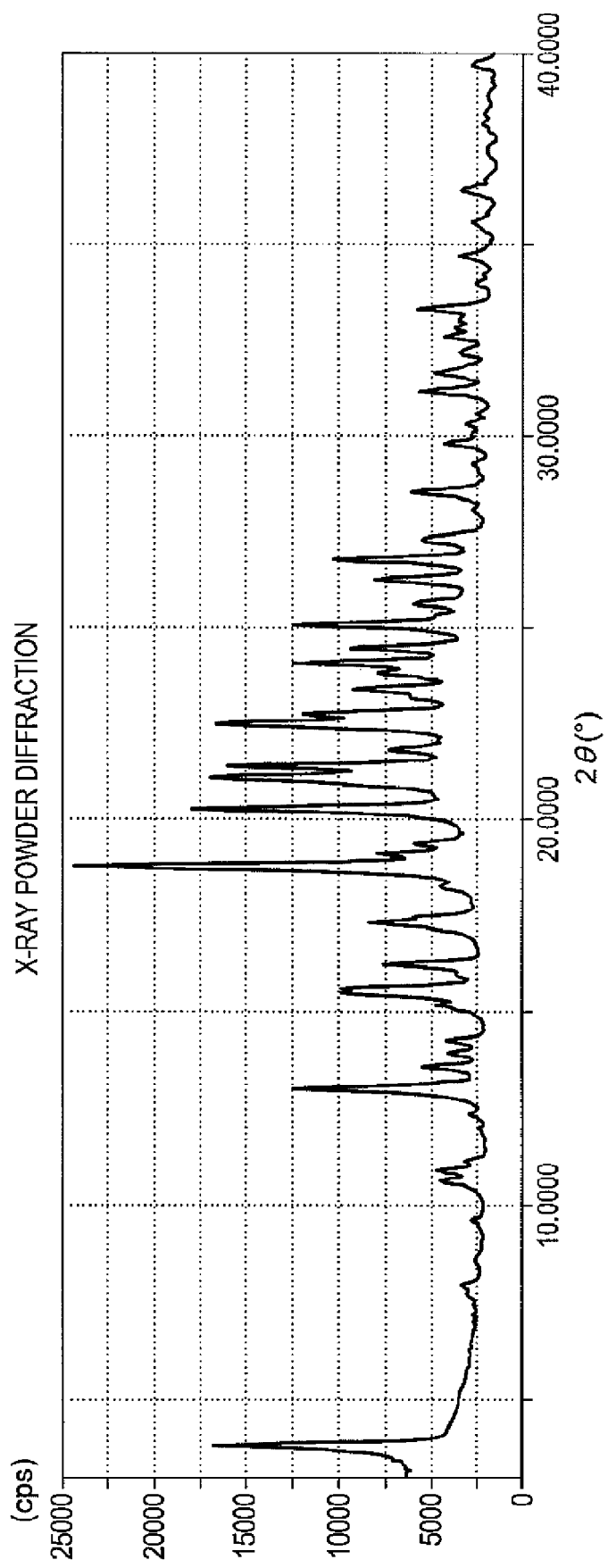
FIG. 1:
X-ray powder diffraction pattern of the crystalline of hemihydrate of the compound of formula (I).
Figure 2:
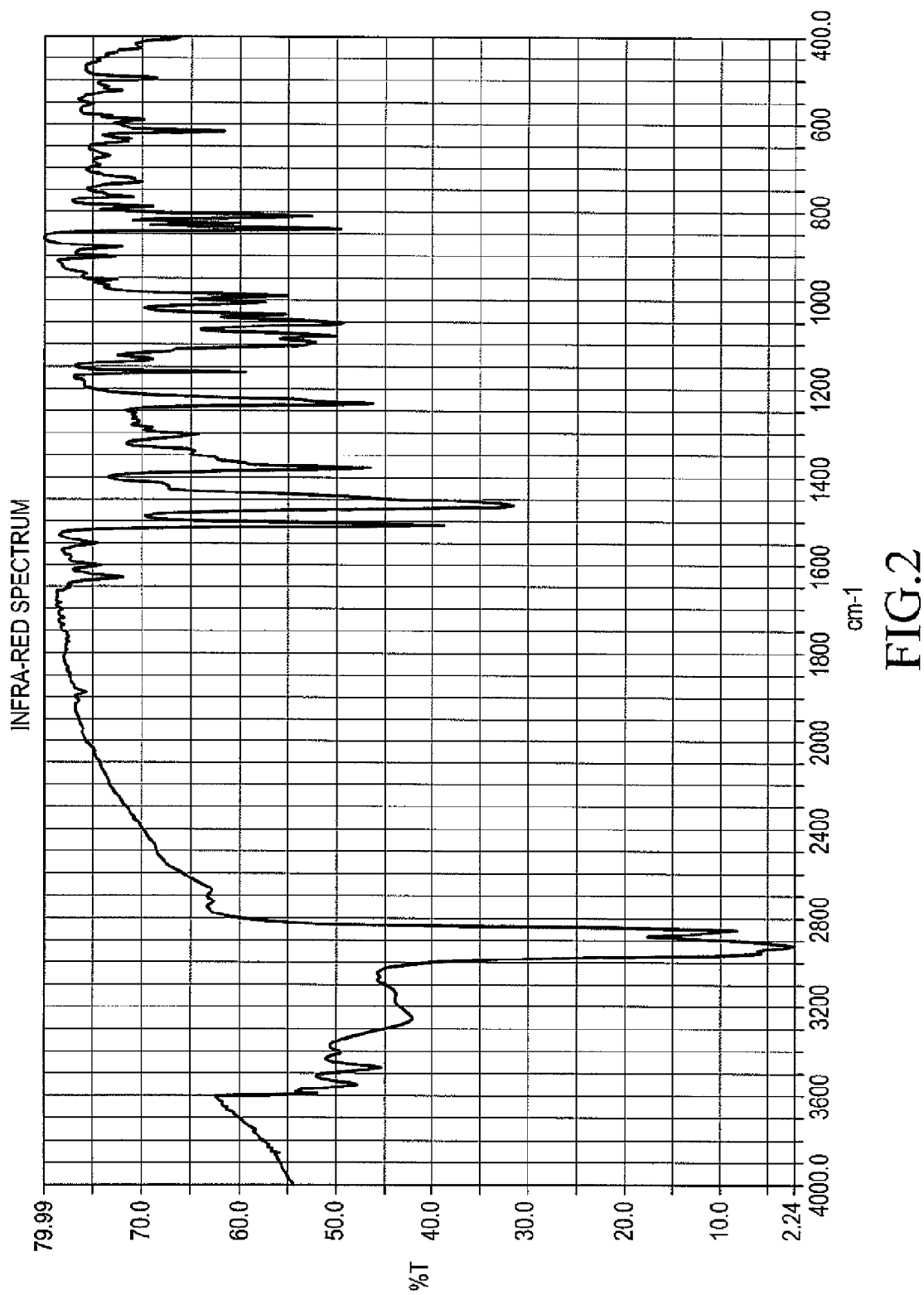
FIG. 2:
Infra-red spectrum of the crystalline of hemihydrate of the compound of formula (I).

Accordingly, the present invention is directed to:

1. A crystalline of hemihydrate of 1-(β-D-glucopyranosyl)-4-methyl-3-[5-(4-fluorophenyl)-2-thienylmethyl]benzene.
2. A crystalline of hemihydrate of 1-(β-D-glucopyranosyl)-4-methyl-3-[5-(4-fluorophenyl)-2-thienylmethyl]benzene characterized by a powder x-ray diffraction pattern comprising the following 2θ values measured using CuK$_\alpha$ radiation: 4.36±0.2, 13.54±0.2, 16.00±0.2, 19.32±0.2, 20.80±0.2.
3. A crystalline of hemihydrate of 1-(β-D-glucopyranosyl)-4-methyl-3-[5-(4-fluorophenyl)-2-thienylmethyl]benzene, having substantially the same X-ray powder diffraction pattern as set out in FIG. 1.
4. A crystalline of hemihydrate of 1-(β-D-glucopyranosyl)-4-methyl-3-[5-(4-fluorophenyl)-2-thienylmethyl]benzene, having substantially the same IR spectrum, as set out in FIG. 2.
5. A process for the preparation of a crystalline of hemihydrate of 1-(β-D-glucopyranosyl)-4-methyl-3-[5-(4-fluorophenyl)-2-thienylmethyl]benzene, which comprises forming a solution of 1-(β-D-glucopyranosyl)-4-methyl-3-[5-(4-fluorophenyl)-2-thienylmethyl]benzene and crystallizing said hemihydrate from the solution by precipitation or recrystallization.
6. A pharmaceutical composition comprising an effective amount of a crystalline of hemihydrate of 1-(β-D-glucopyranosyl)-4-methyl-3-[5-(4-fluorophenyl)-2-thienylmethyl]benzene and a pharmaceutically acceptable carrier.
7. A method for treatment or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises administering a therapeutically effective amount of a crystalline of hemihydrate of 1-(β-D-glucopyranosyl)-4-methyl-3-[5-(4-fluorophenyl)-2-thienylmethyl]benzene.

As discussed, the present invention includes a certain solid state crystalline form. Several methods for characterizing such forms exist, and the invention should not be limited by the methods chosen or the instrumentation used in characterizing the compounds of the present invention. For example, with regard to x-ray diffraction patterns, the diffraction peak intensities in the experimental patterns can vary, as is known in the art, primarily due to preferred orientation (non-random orientation of the crystals) in the prepared sample. As such, the scope of the present invention must be considered in light of the variability of characterization that is appreciated by those skilled in the art.

X-Ray Powder Diffraction

The crystalline form of the present invention (I) is characterized by its X-ray powder diffraction pattern. The X-ray diffraction pattern of the crystalline of hemihydrate of the compound (I) was measured on an X-ray diffractometer (RINT-TTR III, Rigaku, Tokyo, Japan) with measured using $CuK_\alpha$ radiation. Methodology of X-ray powder diffraction is as follows:

Scanning rate: 2.00 degree/minute.
Target: $CuK_\alpha$.
Voltage: 50 kV.
Current: 300 mA.
Scan range: from 3 to 40.0 degree.
Sampling width: 0.0200 degree.

Infra-Red Spectrum

The infra-red spectrum of the crystalline form of the present invention in mineral oil comprises the following main peaks: 1626, 1600, 1549, and 1507 $cm^{-1}$.

The infra-red spectrum of crystalline compound (I) hemihydrate is shown in the accompanying drawing in which the ordinate is the transmittance in % and the abscissa is the wavenumber in $cm^{-1}$.

Thermogravimetric Analysis

The crystalline form of the present invention has been observed to exist in a hemihydrate form. The theoretical water content of the crystalline of the present invention is 1.98%. The thermogravimetric analysis for the crystalline of the present invention shows a mass loss of 1.705%.

Methodology of thermogravimetric analysis is as follows: about 8 mg of compound (I) hemihydrate is weighed and transferred in an aluminum cell holder for TG-50 (Shimadzu, Japan), and then, the thermogravimetric (TG) thermal curve of crystalline compound (I) hemihydrate is determined at a heat rate of 5° C./minute. Typical measuring range is from ambient to 150° C.

The present invention also provides a process for producing the crystalline form of hemihydrate of the compound (I) which comprises forming a solution of compound (I) and precipitating the crystalline form from solution.

Typically, the crystalline of hemihydrate of the compound (I) may be obtained from a mixture of the compound of formula (I), a good solvent and water, optionally containing a poor solvent.

Sometimes some impurities may act as crystallization inhibitors, and impurities need to be removed using a conventional manner, such as silica gel column chromatography. However, the crystalline of hemihydrate of the compound of formula (I) can even be obtained from relatively impure compound (I).

The present invention also provides a pharmaceutical composition comprising the crystalline of hemihydrate of the compound (I) and a pharmaceutically acceptable carrier.

The crystalline compound of the present invention possesses activity as inhibitors of sodium-dependent glucose transporters, and show excellent blood glucose lowering effect.

The crystalline form of the present invention are expected to be useful in the treatment, prevention or delaying the progression or onset of diabetes mellitus (type 1 and type 2 diabetes mellitus, etc.), diabetic complications (such as diabetic retinopathy, diabetic neuropathy, diabetic nephropathy), postprandial hyperglycemia, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, atherosclerosis, or hypertension.

The crystalline form of the present invention or a pharmaceutically acceptable salt thereof may be administered either orally or parenterally, and can be used in the form of a suitable pharmaceutical preparation. Suitable pharmaceutical preparations for oral administration include, for example, solid preparations such as tablets, granules, capsules, and powders, or solution preparations, suspension preparations, emulsion preparations, and the like. Suitable pharmaceutical preparations for parenteral administration include, for example, suppositories; injection preparations or intravenous drip preparations, using distilled water for injection, physiological saline solution or aqueous glucose solution; and inhalant preparations.

The pharmaceutical compositions herein will contain, per dosage unit, e.g., tablet, capsule, powder, injection, suppository, teaspoonful and the like, from about 0.01 mg/kg to about 100 mg/kg body weight (preferably from about 0.01 mg/kg to about 50 mg/kg; and, more preferably, from about 0.01 mg/kg to about 30 mg/kg) of the active ingredient, and may be given at a dosage of from about 0.01 mg/kg/day to about 100 mg/kg/day (preferably from about 0.01 mg/kg/day to about 50 mg/kg/day and more preferably from about 0.01 mg/kg/day to about 30 mg/kg/day). The method of treating a disorder described in the present invention may also be carried out using a pharmaceutical composition comprising the crystalline form as defined herein and a pharmaceutical acceptable carrier. The dosage form will contain from about 0.01 mg/kg to about 100 mg/kg (preferably from about 0.01 mg/kg to about 50 mg/kg; and, more preferably, from about 0.01 mg/kg to about 30 mg/kg) of the active ingredient, and may be constituted into any form suitable for the mode of administration selected. The dosages, however, may be varied depending upon administration routes, the requirement of the subjects, the severity of the condition being treated and the compound being employed. The use of either daily administration or post-periodic dosing may be employed.

The crystalline form of the present invention may be used, if necessary, in combination with one or more of other antidiabetic agents, antihyperglycemic agents and/or agents for treatment of other diseases. The present compounds and these other agents may be administered in the same dosage form, or in a separate oral dosage form or by injection.

The dosage of those agents may vary according to, for example, ages, body weight, conditions of patients, administration routes, and dosage forms.

These pharmaceutical compositions may be orally administered to mammalian species including human beings, apes, and dogs, in the dosage form of, for example, tablet, capsule, granule or powder, or parenterally administered in the form of injection preparation, or intranasally, or in the form of transdermal patch.

The crystalline form of hemihydrate of the compound of formula (I) can be prepared from a mixture of the compound (I), a good solvent and water, optionally containing a poor solvent.

Examples of good solvents which have been found suitable include ketones (e.g., acetone, 2-butanone), esters (e.g., ethyl acetate, methyl acetate), alcohols (e.g., methanol, ethanol, i-propanol), and a mixture of these solvents. Examples of poor solvents include alkanes (e.g., hexane, heptane), aromatic hydrocarbons (e.g., benzene, toluene), ethers (e.g., diethyl ether, dimethyl ether, diisopropyl ether) and a mixture of these solvents.

One preferred preparation of the crystalline form of hemihydrate of the compound of formula (I) typically involves dissolving in a good solvent (e.g., ketones or esters) crude or amorphous compound of formula (I) prepared in accordance with the procedures described in WO 2005/012326 pamphlet, and adding water and a poor solvent (e.g., alkanes or ethers) to the resulting solution, followed by filtration.

In case that a good solvent is soluble in water, a poor solvent needs not be used and water may be added to the solution of the compound of formula (I) in the good solvent so the solubility of the compound of formula (I) can be decreased in the solution.

In case that a poor solvent is used, water is preferably used in amount of 1 to 10 molar equivalents to the compound of formula (I), the good solvent is preferably used in amount of 10 to 100 times of volume of water, and the poor solvent is preferably used in amount of 0.1 to 10 times of volume of the good solvent.

The precise conditions under which the crystalline of hemihydrate of the compound (I) is formed may be empirically determined.

Under these conditions, crystallization can preferably be carried out at a lowered, ambient or elevated temperature.

The crystalline form of hemihydrate of the compound of formula (I) is significantly easier to isolate than amorphous form of the compound and can be filtered from the crystallization medium after cooling, and washed and dried. Also, the crystalline form of the present invention is more stable than the amorphous form of the compound of formula (I).

EXAMPLES

Example 1

Crystalline 1-(β-D-glucopyranosyl)-4-methyl-3-[5-(4-fluorophenyl)-2-thienylmethyl]benzene hemihydrate 1-(β-D-glucopyranosyl)-4-methyl-3-[5-(4-fluorophenyl)-2-thienylmethyl]benzene was prepared in a similar manner as described in WO 2005/012326.

(1) To a solution of 5-bromo-1-[5-(4-fluorophenyl)-2-thienylmethyl]-2-methylbenzene (1, 28.9 g) in tetrahydrofuran (480 ml) and toluene (480 ml) was added n-butyllithium (1.6M hexane solution, 50.0 ml) dropwise at −67 to −70° C.

under argon atmosphere, and the mixture was stirred for 20 minutes at the same temperature. Thereto was added a solution of 2 (34.0 g) in toluene (240 ml) dropwise at the same temperature, and the mixture was further stirred for 1 hour at the same temperature. Subsequently, thereto was added a solution of methanesulfonic acid (21.0 g) in methanol (480 ml) dropwise, and the resulting mixture was allowed to warm to room temperature and stirred for 17 hours. The mixture was cooled under ice—water cooling, and thereto was added a saturated aqueous sodium hydrogen carbonate solution. The mixture was extracted with ethyl acetate, and the combined organic layer was washed with brine and dried over magnesium sulfate. The insoluble was filtered off and the solvent was evaporated under reduced pressure. The residue was triturated with toluene (100 ml)—hexane (400 ml) to give 1-(1-methoxyglucopyranosyl)-4-methyl-3-[5-(4-fluorophenyl)-2-thienylmethyl]-benzene (3) (31.6 g). APCI-Mass m/Z 492 (M+NH$_4$).

(2) A solution of 3 (63.1 g) and triethylsilane (46.4 g) in dichloromethane (660 ml) was cooled by dry ice-acetone bath under argon atmosphere, and thereto was added dropwise boron trifluoride•ethyl ether complex (50.0 ml), and the mixture was stirred at the same temperature. The mixture was allowed to warm to 0° C. and stirred for 2 hours. At the same temperature, a saturated aqueous sodium hydrogen carbonate solution (800 ml) was added, and the mixture was stirred for 30 minutes. The organic solvent was evaporated under reduced pressure, and the residue was poured into water and extracted with ethyl acetate twice. The organic layer was washed with water twice, dried over magnesium sulfate and treated with activated carbon. The insoluble was filtered off

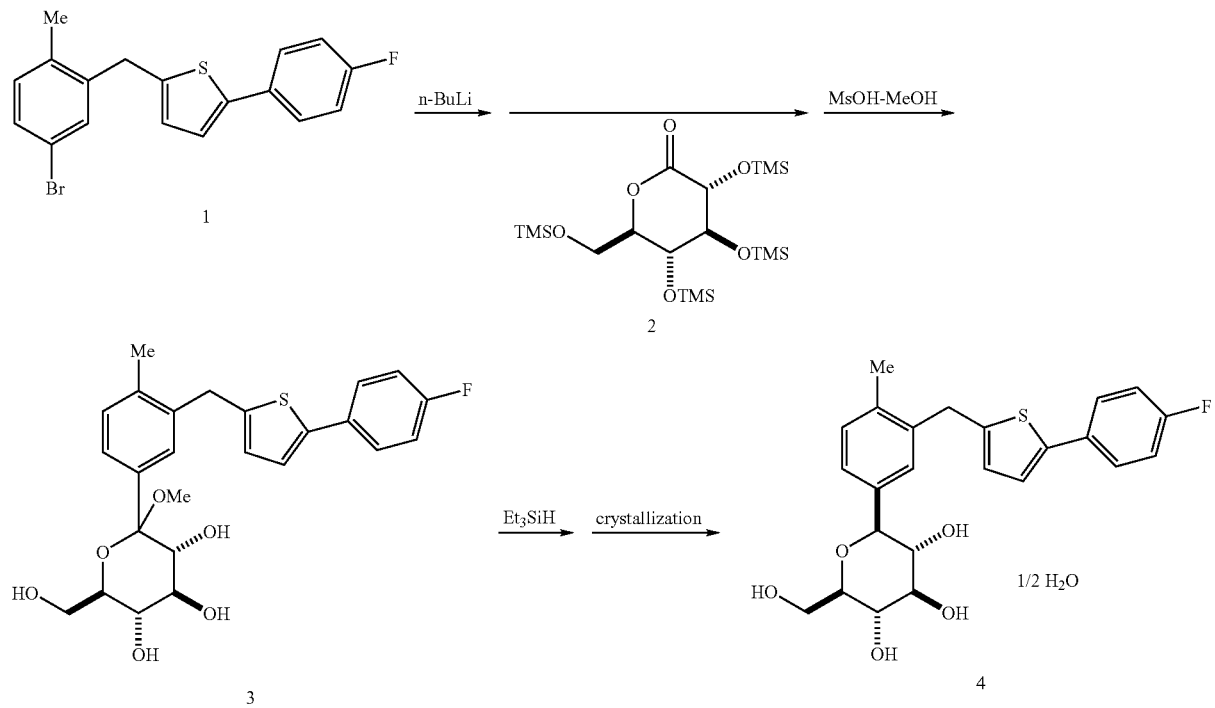

and the solvent was evaporated under reduced pressure. The residue was dissolved in ethyl acetate (300 ml), and thereto were added diethyl ether (600 ml) and H$_2$O (6 ml). The mixture was stirred at room temperature overnight, and the precipitate was collected, washed with ethyl acetate-diethyl ether (1:4) and dried under reduced pressure at room temperature to give 1-(β-D-glucopyranosyl)-4-methyl-3-[5-(4-fluorophenyl)-2-thienylmethyl]benzene hemihydrate (33.5 g) as colorless crystals. mp 98-100° C. APCI-Mass m/Z 462 (M+NH$_4$). $^1$H-NMR (DMSO-d$_6$) δ 2.26 (3H, s), 3.13-3.28 (4H, m), 3.44 (1H, m), 3.69 (1H, m), 3.96 (1H, d, J=9.3 Hz), 4.10, 4.15 (each 1H, d, J=16.0 Hz), 4.43 (1H, t, J=5.8 Hz), 4.72 (1H, d, J=5.6 Hz), 4.92 (2H, d, J=4.8 Hz), 6.80 (1H, d, J=3.5 Hz), 7.11-7.15 (2H, m), 7.18-7.25 (3H, m), 7.28 (1H, d, J=3.5 Hz), 7.59 (2H, dd, J=8.8, 5.4 Hz). Anal. Calcd. for C$_{24}$H$_{25}$FO$_5$S.0.5H$_2$O: C, 63.56; H, 5.78; F, 4.19; S, 7.07. Found: C, 63.52; H, 5.72; F, 4.08; S, 7.00.

Example 2

An amorphous powder of 1-(β-D-glucopyranosyl)-4-methyl-3-[5-(4-fluorophenyl)-2-thienylmethyl]benzene (1.62 g) was dissolved in acetone (15 ml), and thereto were added H$_2$O (30 ml) and a crystalline seed. The mixture was stirred at room temperature for 18 hours, and the precipitate was collected, washed with acetone—H$_2$O (1:4, 30 ml) and dried under reduced pressure at room temperature to give 1-(β-D-glucopyranosyl)-4-methyl-3-[5-(4-fluorophenyl)-2-thienylmethyl]benzene hemihydrate (1.52 g) as colorless crystals. mp 97-100° C.

The invention claimed is:

1. A crystalline form of 1-(β-D-glucopyranosyl)-4-methyl-3-[5-(4-fluorophenyl)-2-thienylmethyl]benzene hemihydrate.

2. A crystalline form of 1-(β-D-glucopyranosyl)-4-methyl-3-[5-(4-fluorophenyl)-2-thienylmethyl]benzene hemihydrate of claim 1, having a powder x-ray diffraction pattern comprising the following 2θ values measured using CuK$_α$ radiation: 4.36±0.2, 13.54±0.2, 16.00±0.2, 19.32±0.2, and 20.80±0.2.

3. A crystalline form of 1-(β-D-glucopyranosyl)-4-methyl-3-[5-(4-fluorophenyl)-2-thienylmethyl]benzene hemihydrate of claim 1, having substantially the same X-ray diffraction pattern as set out in FIG. 1.

4. A crystalline form of 1-(β-D-glucopyranosyl)-4-methyl-3[5-(4-fluorophenyl)-2-thienylmethyl]benzene hemihydrate of claim 1, having substantially the same IR spectrum, as set out in FIG. 2.

5. A process for the preparation of a crystalline form of 1-(β-D-glucopyranosyl)-4-methyl-3-[5-(4-fluorophenyl)-2-thienylmethyl]benzene hemihydrate of claim 1, which comprises forming a solution of 1-(β-D-glucopyranosyl)-4-methyl-3[5-(4-fluoro-phenyl)-2-thienylmethyl]benzene and crystallizing said hemihydrate from the solution by precipitation or recrystallization.

6. A pharmaceutical composition comprising an effective amount of a crystalline form of 1-(β-D-glucopyranosyl)-4-methyl-3-[5-(4-fluorophenyl)-2-thienylmethyl]benzene hemihydrate of claim 1 and a pharmaceutically acceptable carrier.

7. A method for treatment or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises administering a therapeutically effective amount of a crystalline form of 1-(β-D-glucopyranosyl)-4-methyl-3[5-(4-fluorophenyl)-2-thienylmethyl]benzene hemihydrate of claim 1 to a subject in need thereof.

\* \* \* \* \*